United States Patent
Allen et al.

(10) Patent No.: US 6,268,489 B1
(45) Date of Patent: Jul. 31, 2001

(54) AZITHROMYCIN DIHYDRATE

(75) Inventors: Douglas J. M. Allen, New London; Kevin M. Nepveux, Old Saybrook, both of CT (US)

(73) Assignee: Pfizer Inc., New York, NY (US)

(*) Notice: Subject to any disclaimer, the term of this patent is extended or adjusted under 35 U.S.C. 154(b) by 0 days.

(21) Appl. No.: 07/994,040

(22) Filed: Dec. 21, 1992

Related U.S. Application Data

(63) Continuation of application No. 07/449,961, filed on Dec. 11, 1989, now abandoned.

(30) Foreign Application Priority Data

Jul. 9, 1987 (WO) .................................. PCT/US87/01612

(51) Int. Cl.[7] .................................................. C07H 17/08
(52) U.S. Cl. ............................................ 536/7.4; 536/18.5
(58) Field of Search ...................................... 536/7.4, 18.5

(56) References Cited

U.S. PATENT DOCUMENTS

| | | | |
|---|---|---|---|
| 4,020,270 | | 4/1977 | Arcamone et al. .................... 536/18 |
| 4,219,641 | * | 8/1980 | Deposato et al. .................... 536/7.2 |
| 4,474,768 | * | 10/1984 | Bright .................................... 514/29 |
| 4,512,982 | * | 4/1985 | Hauske et al. ....................... 536/7.2 |
| 4,517,359 | | 5/1985 | Kobrehel et al. .................... 536/7.4 |
| 4,526,889 | | 7/1985 | Bright .................................... 514/29 |
| 4,963,531 | | 10/1990 | Remington ............................ 514/29 |

OTHER PUBLICATIONS

Pelizza et al., Farmaco–Ed.Sc., 31, 254–262 (1976).
Allen et al., J. Pharm. Sci., 67, 1087–1093 (1978).

* cited by examiner

*Primary Examiner*—Elli Peselev
(74) *Attorney, Agent, or Firm*—Peter C. Richardson; Gregg C. Benson; Mervin E. Brokke

(57) ABSTRACT

Non-hygroscopic, azithromycin (9-deoxo-9a-aza-9a-methyl-9a-homoerythromycin) dihydrate and a process therefor.

3 Claims, No Drawings

AZITHROMYCIN DIHYDRATE

This is a continuation of application Ser. No. 07/449,961, filed on Dec. 11, 1989 now abandoned as a request for U.S. examination of International Application No. PCT/US87/01612, filed Jul. 9, 1987.

BACKGROUND OF THE INVENTION

The present invention is directed to a valuable new form of azithromycin (9-deoxo-9a-aza-9a-methyl-9a-homoerythromycin A), viz., a non-hygroscopic dihydrate form thereof.

Azithromycin is the U.S.A.N. (generic name) for 9-deoxo-9a-aza-9a-methyl-9a-homoerythromycin A, a broad spectrum antibacterial compound derived from erythromycin A. Azithromycin was independently discovered by Bright, U.S. Pat. No. 4,474,768 and Kobrehel et al., U.S. Pat. No. 4,517,359. The name "N-methyl-11-aza-10-deoxo-10-dihydroerythromycin A" was employed in these patents. The present more systematic name is based upon the ring expansion and replacement nomenclature of the "IUPAC Nomenclature of Organic Chemistry, 1979 Edition," Pergamon Press, 1979, pp. 68–70, 459, 500–503.

As previously crystallized from ethanol and water (e.g., Example 3 of U.S. Pat. No. 4,474,768), azithromycin was obtained as a hygroscopic monohydrate (for details, see Preparation 1 below). Because of its hygroscopic nature, it is most difficult to prepare and maintain this prior monohydrate product in a form having a constant, reproducible water-content. It is particularly difficult to handle during formulation, since at higher relative humidity levels which are generally required to avoid electrostatic problems (e.g., flow rates, dusting with potential for explosion), the monohydrate readily picks up varying amounts of water, the amount depending upon exposure time and the precise value of the relative humidity (see Preparation 1 below). Such problems have been overcome by the present invention of a stable dihydrate which is essentially non-hygroscopic under conditions of relative humidity conducive to formulation of azithromycin.

SUMMARY OF THE INVENTION

The present invention is directed to a valuable new form of azithromycin, viz., a crystalline, non-hygroscopic dihydrate, prepared by crystallization from tetrahydrofuran and an aliphatic ($C_5$–$C_7$)hydrocarbon in the presence of at least two molar equivalents of water.

Azithromycin is of the formula

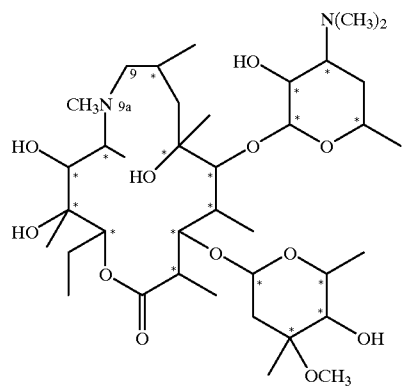

It is derived from erythromycin A without involvement of asymmetric centers, and so has stereochemistry at each of these centers (*) which is identical with that of erythromycin A. Named systematically as an erythromycin A derivative, the compound is called 9-deoxo-9a-aza-9a-methyl-9a-homoerythromycin A. Azithromycin, including the present dihydrate, possess broad-spectrum antibacterial activity useful in the treatment of susceptible bacterial infections in mammals, including man.

The expression "aliphatic ($C_5$–$C_7$)hydrocarbon" refers to lower boiling hydrocarbon solvents, frequently mixtures of particular boiling point ranges such as those generally referred to as "pentane", "hexane", "hexanes", etc., but which may also be substantially pure, e.g., n-hexane, cyclohexane or methylcyclohexane. A preferred hydrocarbon solvent is so-called "hexane", having a boiling point which ranges near that of pure n-hexane.

DETAILED DESCRIPTION OF THE INVENTION

The present invention is readily carried out. Azithromycin, prepared according to Bright or Kobrehel et al. (cited above) in amorphous form, or as the monohydrate (which may contain, because of its hygroscopicity, more than one molar equivalent of water) is dissolved in tetrahydrofuran. Since the temperatures required for the initial stages of the present process are not critical, ambient temperatures are generally employed, avoiding the cost of heating and cooling. Furthermore, to maximize yield and minimize solvent, labor and equipment costs, the volume of tetrahydrofuran is kept to a near minimum, e.g., 2 liters of solvent per kilogram of substrate. Any insoluble impurities which may be present at this stage are readily removed by conventional methods of filtration. If necessary, the mixture can be decolorized with activated carbon. If desired, the highly concentrated mixture can be diluted with a portion of ($C_5$–$C_7$)hydrocarbon prior to filtration, in order to facilitate handling. If the water content of the ingoing bulk is much greater than one molar equivalent, e.g., approaching 2-molar equivalents, it is preferable to dry the mixture for a short period of time over a drying agent such as $MgSO_4$, particularly if hydrocarbon solvent is to be added prior to filtration. To obtain the crystalline dihydrate, water is added to the resulting clear solution, in an amount sufficient to bring the total water content to a level corresponding to at least two molar equivalents, generally not exceeding a level of about 3–4 molar equivalents. The level of water present in the system is readily monitored by standard Karl Fischer titration. The addition of water is followed by the addition of the hydrocarbon solvent (or of more hydrocarbon solvent, if the mixture was previously diluted before filtration), leading to crystallization of the desired dihydrate product. This stage of the process can be carried out at ambient temperature (e.g. 17–30° C.), but to facilitate the initial crystallization, is preferably carried at slightly elevated temperature (e.g. 30–40° C.). The total volume of hydrocarbon solvent employed is generally at least about four times in volume that of the tetrahydrofuran. Higher volumes of hydrocarbon are satisfactory, but are generally avoided in the interest of minimizing cost. Once crystallization is complete, the product is recovered by filtration, usually after a period of granulation (e.g., 3–24 hours) at ambient temperature. The product is usually vacuum dried of organic solvents (at 20–40° C., conveniently at ambient temperature). To avoid loss of water of hydration, the volatiles and water-content are generally monitored during drying, such that the level of tetrahydrofuran and hydrocarbon will generally fall below 0.25% and the water content will be within 0.3% of theory (4.6%).

Azithromycin dihydrate is formulated and administered in the treatment of susceptible bacterial infections in man according to methods and in amounts previously detailed by Bright, U.S. Pat. No. 4,474,768, cited above and hereby incorporated by reference.

The present invention is illustrated by the following examples. However, it should be understood that the invention is not limited to the specific details of these examples.

EXAMPLE 1

Non-Hygroscopic Azithromycin Dihydrate

Method A

The hygroscopic monohydrate of Preparation 1 (100 g; water-content:3.1%), tetrahydrofuran (220 ml) and diatomaceous earth (5 g) were combined in a 500 ml Erlenmyer flask, stirred for 30 minutes and filtered with 20 ml of tetrahydrofuran wash. The combined filtrate and wash was transferred to a 3 liter round bottom flask. The solution was stirred vigorously and $H_2O$ (2.0 ml) was added. After 5 minutes, hexane (1800 ml) was added over 5 minutes, with continued vigorous stirring. Following an 18 hour granulation period, title product was recovered by filtration with 1×10 ml hexane wash, and dried in vacuo to 4.6±0.2% $H_2O$ by Karl Fischer, 89.5 g.

Method B

The hygroscopic monohydrate of Preparation 1 (197.6 g) and tetrahydrofuran (430 ml) were charged to a reactor and the mixture stirred to achieve a milky white solution. Activated carbon (10 g) and diatomaceous earth (10 g) were added and the mixture stirred for 15 minutes, then diluted with 800 ml of hexane and filtered with suction over a pad of diatomaceous earth with 250 ml of hexane for wash. The combined filtrate and wash was diluted to 2500 ml with hexane and warmed to 34° C. With stirring, 24.7 ml of $H_2O$ was added. The mixture was allowed to cool to room temperature, granulated for five hours and title product recovered and dried as in Method A, 177.8 g.

The dihydrate melts sharply at 126° C. (hot stage, 10°/minute); differential scanning calorimetry (heating rate, 20° C./minute) shows an endotherm at 127° C.; thermal gravimetric analysis (heating rate 30° C./minute) shows a 1.8% weight loss at 100° C. and a 4.3% weight loss at 150° C.; ir (KBr) 3953, 3553, 3488, 2968, 2930, 2888, 2872, 2827, 2780, 2089, 1722, 1664, 1468, 1426, 1380, 1359, 1344, 1326, 1318, 1282, 1270, 1252, 1187, 1167, 1157, 1123, 1107, 1082, 1050, 1004, 993, 977, 955, 930, 902, 986, 879, 864, 833, 803, 794, 775, 756, 729, 694, 671, 661, 637, 598, 571, 526, 495, 459, 399, 374, 321 and 207 cm$^{-1}$; [alpha]$^{26}_D$=41.4° (c=1, CHCl$_3$).

Anal. Calcd. for $C_{38}H_{72}N_2O_{12} \cdot 2H_2O$: C, 58.14; H, 9.77; N, 3.57; OCH$_3$, 3.95; $H_2O$, 4.59. Found: C, 58.62; H, 9.66; N, 3.56; OCH$_3$, 4.11; $H_2O$, 4.49. Neutralization Equivalent (0.5N HCl in 1:1 CH$_3$CN:H$_2$O): Calcd.: 374.5. Found: 393.4.

Samples of a dihydrate, slightly over dried to contain 4.1% water (less than theoretical) rapidly picked-up water at 33%, 75% or 100% relative humidities to achieve the theoretical water content (4.6%) for the dihydrate. At 33% and 75% relative humidities, water content remained essentially constant for at least 4 days. At 100% relative humidity, the water content further rose to about 5.2, where it remained essentially constant of the next three days.

A sample of the same dihyrate, maintained at 18% relative humidity gradually lost water. At four days, the water content was 2.5% and at 12 days, 1.1%.

PREPARATION 1

Hygroscopic Azithromycin Monohydrate

Substantially following the methylation procedure of Kobrehel et al., U.S. Pat. No. 4,517,359; and the crystallization procedure of Bright, U.S. Pat. No. 4,474,768; 9-deoxo-9a-aza-9a-homoerythromycin A (previously called 11-aza-10-deoxo-10-dihydroerythromycin A; 100 g, 0.218 mol) was dissolved with stirring in 400 ml CHCl$_3$. Formic acid (98%; 10.4 ml, 0.436 mol) and formaldehyde (37%; 16.4 ml, 0.349 mol) were added over 4–5 minutes, and the mixture heated at reflux for 20 hours. The mixture was cooled to ambient temperature, diluted with 400 ml $H_2O$ and adjusted to pH 10.5 with 50% NaOH. The aqueous layer was separated and extracted 2×100 ml with fresh CHCl$_3$. The organic layers were combined, stripped in vacuo to 350 ml, twice diluted with 450 ml of ethanol and restripped to 350 ml, and finally diluted with 1000 ml $H_2O$ over a 1 hour period, pausing for 15 minutes as a slurry began to develop after the addition of about 250 ml of $H_2O$. Title product was recovered by filtration and dried in air at 50° C. for 24 hours, 85 g; mp 136° C.; differential thermal analysis (heating rate 20° C./minute) shows an endotherm at 142° C.; thermal gravimetric analysis (heating rate 30° C./minute) shows a 2.6% weight loss at 100° C. and a 4.5% weight loss at 150° C.; water content 3.92%; ethanol content 1.09%.

Anal. Calcd. for $C_{38}H_{72}N_2O_{12}$ (corrected for ethanol and water content): C, 58.46; H, 9.78; N, 3.74; Alkoxy, 4.67. Found: C, 58.40; H, 9.29; N, 3.50; Alkoxy, 4.52.

A sample of the monohydrate (having a water content of 3.2%) was maintained at 18% relative humidity for 14 days. The sample lost water over the first 24 hours to yield monohydrate having the theoretical water content (2.35%). The water content then remained substantially constant over 14 days, a value of 2.26% being recorded at 14 days.

At 33% relative humidity the water content of a sample of the same monohydrate rapidly rose to 5.6% where it remained substantially steady for at least three days. Similarly at 75% and 100% relative humidity, the water content rose rapidly, but was now maintained at even higher levels, 6.6% and 7.2%, respectively, for at least 3 days.

What is claimed is:

1. Crystalline azithromycin dihydrate.

2. A method of preparing crystalline azithromycin dihydrate which comprises crystallization of amorphous azithromycin or azithromycin monohydrate from a mixture of tetrahydrofuran and a ($C_5$–$C_7$) aliphatic hydrocarbon in the presence of at least 2 molar equivalents of water.

3. A method of claim 2 wherein the hydrocarbon is hexane.

* * * * *